United States Patent
Tang et al.

(10) Patent No.: US 11,506,648 B2
(45) Date of Patent: Nov. 22, 2022

(54) DETECTION METHOD FOR QUALITY GRADE OF TRADITIONAL CHINESE MEDICINE

(71) Applicant: Shaanxi University of Chinese Medicine, Xianyang (CN)

(72) Inventors: Zhishu Tang, Xianyang (CN); Yanru Liu, Xianyang (CN); Zhongxing Song, Xianyang (CN); Dahai Jiang, Xianyang (CN); Ningjuan Yang, Xianyang (CN); Aibing Chang, Xianyang (CN); Xiaohong Li, Xianyang (CN)

(73) Assignee: SHAANXI UNIVERSITY OF CHINESE MEDICINE, Xianyang (CN)

( * ) Notice: Subject to any disclaimer, the term of this patent is extended or adjusted under 35 U.S.C. 154(b) by 245 days.

(21) Appl. No.: 16/913,597

(22) Filed: Jun. 26, 2020

(65) Prior Publication Data

US 2021/0055276 A1 Feb. 25, 2021

(30) Foreign Application Priority Data

Aug. 20, 2019 (CN) .......................... 201910769351.1

(51) Int. Cl.
| | |
|---|---|
| *G01N 33/15* | (2006.01) |
| *G16H 20/90* | (2018.01) |
| *G06F 17/18* | (2006.01) |
| *G06K 9/62* | (2022.01) |

(52) U.S. Cl.
CPC ............. *G01N 33/15* (2013.01); *G06F 17/18* (2013.01); *G06K 9/6219* (2013.01); *G16H 20/90* (2018.01)

(58) Field of Classification Search
CPC ............................... G01N 33/15; G16H 20/90
See application file for complete search history.

(56) References Cited

U.S. PATENT DOCUMENTS

2005/0003030 A1* 1/2005 Simon .................. A61K 36/185
424/769

FOREIGN PATENT DOCUMENTS

WO    WO-2011113066 A1 *   9/2011   ............. G01N 27/62

* cited by examiner

*Primary Examiner* — Ruiping Li
(74) *Attorney, Agent, or Firm* — Brian S. Boyer; Syndicated Law, PC

(57) ABSTRACT

Disclosed is a detection method for quality grade of traditional Chinese medicine (TCM), including: detecting the levels of quality control index components of TCM and efficacy-related in vitro activity by establishing a correlation between principal components of TCM and in vitro activity; determining the state of sample cluster by principal component analysis; constructing a logistic regression model of quality grade versus index components and bioactivity and establishing corresponding grade detection formulas of Chinese medicinal materials by fitting a large number of sample data for Chinese medicinal materials from different places of origin and batches. The method of the present invention realizes the mathematical expression of a standard for quality difference of TCM, and provides a feasible solution for the industrialized evaluation of quality grades of Chinese medicinal materials or herbal slices finally.

8 Claims, 1 Drawing Sheet

DETECTION METHOD FOR QUALITY GRADE OF TRADITIONAL CHINESE MEDICINE

CROSS REFERENCE TO RELATED APPLICATION

This application claims the priority benefit of Chinese Patent Application No. 201910769351.1, filed Aug. 20, 2019, which is hereby incorporated herein by reference in its entirety.

TECHNICAL FIELD

The present invention designs a detection method for quality grade of traditional Chinese medicine (TCM), particularly relates to a detection method of quality grade of TCM based on a "component-efficacy" interaction, and belongs to the technical field of detection of TCM.

BACKGROUND

TCM resources, as national strategic resources, are the material basis for the existence and development of the TCM cause and industry. Therefore, "a perfect TCM standardization evaluation system" is an important means to get rid of the existing dilemmas, e.g., uneven quality and sources of TCM, single quality control method of TCM, and unstable level of efficacy of TCM. Standardization of quality of TCM is an important foundation of TCM industry construction and a key "pioneer" of the development of the TCM industry. Therefore, establishment of a set of scientific research and evaluation methods for Chinese medicinal materials/herbal slices helps perfect a TCM quality control system, strengthen the quality management of TCM, and push ahead with the building of a TCM standardization system.

Grade evaluation of TCM is a promising innovative technology of quality evaluation of TCM. So far, there are evaluation systems of grades and specifications for TCM established based on aesthesiology (appearance and properties), chemical components, bioactivity, etc., and novel, fast and high-resolution quantification techniques of characteristic indexes are developed accordingly, including bio-recognition, molecular identification, and high resolution mass spectrometry. However, TCM production is influenced by complex and ever-changing natural and human factors, and most of sensory, chemical, and activity indexes are not correlated linearly with grades of TCM. Therefore, single and parallel evaluation methods are difficult to evaluate the grades of TCM on the whole and unable to realize a method for determining quality grades of TCM during industrialization.

Factors influencing Chinese medicinal materials/herbal slices are principally classified into three classes: Class 1 is bioactivity: such as in vitro antioxidant activity and in vivo anticoagulant activity; Class 2 is quality control content of a principal component; and Class 3 is composition proportion of all compounds in a fingerprint. It is necessary to use a classification standard for Chinese medicinal materials/herbal slices to generate data as a modeling basis, because establishment of a prediction model and determination of parameters are data-driven. Therefore, excellent (I), good (II), fair (III), and poor (IV) are assigned to response values 4, 3, 2, and 1, respectively.

Chinese medicinal materials/herbal slices are graded in order to select stable quantitative indexes. First of all, principal component analysis (PCA) is used to conduct hierarchical cluster analysis (HCA) and factor analysis on sample data. High-contribution bioactivity and chemical indexes are used as observation factors. Differences in components and activity of Chinese medicinal materials/herbal slices are reflected by using a data processing technology combining PCA with HCA. Classification status of Chinese medicinal materials/herbal slices can be observed preliminarily by classifying different batches of Chinese medicinal materials/herbal slices according to according to activity and components.

PCA is a multivariate statistical analysis that conducts dimension reduction on multidimensional data to simplify a few uncorrelated comprehensive indexes (principal components). Specific modeling process thereof is as follows:

(1) Data preprocessing. Assume there are n samples (i=1, 2, ..., and m) and n indexes (j=1, 2, ..., and n). The original data $X=(x_i^*j)_{m \times n}$ is equalized, which may retain the variation information in the data.

$$X_{ij} = X^*_{ij} / \overline{X}^*_j \quad (1)$$

where: $X^*_{ij}$ is the original data, $\overline{X}^*_j$ is an average of index j, and $X_{ij}$ is a result of data equalization.

(2) Calculation of a covariance matrix of the equalization data: $S=(S_{ij})_{n \times n}$.

(3) Calculation of eigenvalues and eigenvectors of the covariance matrix. n eigenvalues of S are expressed as: $\lambda_1 \geq \lambda_2 \geq \ldots \geq \lambda_n$. If a normalized eigenvector is $a_{jj}=(a_{j1}, a_{j2}, \ldots,$ and $a_{jn})$, then the j-th principal component of the i-th sample is $$F_{ij} = \Sigma_{j=1}^n a_{jj} x_{ij} \quad (2)$$

(4) Determination of the number of principal components. If accumulative variance contribution reaches 85%, the first k principal components can be used as comprehensive evaluation indexes. If $\lambda_1 / \Sigma_{j=1}^n \lambda_j > 0.85$, the first principal component can be used as a comprehensive evaluation index.

Logistic regression, also known as Logit regression, belongs to a probabilistic nonlinear regression model, and is a multivariable analysis method for investigating the relationship between observed classification results. The fundamental principle thereof is to use Logit transformation to establish a linear regression model based on a curve relationship between variable and dependent variable, so as to predict log odds of measured values with results of predictive values. From the viewpoint of the generality and practicality of the model, models with some mathematical expressions are easier to understand and apply. In the logistic regression model, however, a binary model expresses a training sample as "yes" or "no" merely, and the result is that a precisely calculated score can be obtained; ideally, a prediction result can be obtained as long as test set data are input in a mathematical expression established based on the training set. From the viewpoint of the grade prediction, a binary logistic regression model is more suitable to evaluate the grade classification of Chinese medicinal materials/herbal slices.

An objective of the logistic regression analysis is to establish an empirical expression, so as to predict the probability distribution of a dependent variable from an independent variable. Let y=1, 2, 3, 4 denote four grades of TCM. Let $q_1=p(y \leq 1)$, $q_2=p(y \leq 2)$, ..., $q_3=p(y \leq 3)$, then a common logistic regression model is:

$$\ln \frac{q_i}{1-q_i} = \beta_{i0} + \beta_1 x_1 + \cdots + \beta_n x_n \quad (3)$$

where: $\beta_{i0}$ is an intercept, i=1, 2, . . . , and 4; $\beta_1$, . . . , and $\beta_n$ are slope coefficients; $x_1$, . . . , and $x_n$ are independent variables. $\beta_{i0}$, $\beta_1$, . . . and $\beta n$ can be estimated from the existing observed values. Thus, an expression of probability (p) of each grade of Salviae Miltiorrhizae Radix et Rhizoma slices fed is:

$$p_i = \exp(\beta_{i0} + \beta_1 x_1 + \ldots \beta_n x_n)/[1 + \exp(\beta_{i0} + \beta_1 x_1 + \ldots \beta_n x_n)] \quad (4)$$

At this point, forgiven values of independent variables x1, . . . , and xn, q1, q2, and q3 can be predicted by the regression equation; then, the probability of each grade of Salviae Miltiorrhizae Radix et Rhizoma feeding materials can be predicted by p (y=1)=q1, p (y=2)=q2−q1, . . . , and p (y=3)=q3−q2, and p (y=4)=1q3. The category of response variable can be determined by $$p(y = l) = \max_{i=1}^{k} p(y = i).$$

Therefore, the solution of the present invention is a detection method for quality grade of TCM based on a "component-efficacy" interaction. Combining PCA with the binary logistic regression model, the method principally describes mapping relationships between grades of Chinese medicinal materials/herbal slices and influencing factors (chemical components and bioactivity), so as to establish mathematical expressions of quality grades of Chinese medicinal materials/herbal slices. Finally, these expressions will be used to realize the industrial detection of quality grade of TCM directly.

SUMMARY

An objective of the present invention is to provide a method for detecting and determining the quality grade of traditional Chinese medicine (TCM).

Specifically, the objective of the present invention is achieved through the following technical solution:
a detection method for quality grade of TCM, where: the TCM may be Chinese medicinal materials or herbal slices; the detection method is established by constructing a model of correlation between bioactivity and component of TCM.

Further, the detection method for quality grade of TCM includes the following steps: (1) TCM test sample preparation and determination of component assay; (2) bioactivity assay for TCM; (3) principal component assay for TCM; and (4) establishment of TCM quality grade detection formulas by a logistic regression model.

Further, step (1) is specifically as follows:
sample preparation: weighing approximately 0.3 g of Chinese medicinal materials or herbal slices accurately in a conical flask with cover, accurately adding 50 mL of methanol thereto, sealing tightly, weighing, sonicating for 30 min, cooling, weighing again, making up for a weight loss with methanol, shaking well, filtering, and collecting a subsequent filtrate as a sample solution;
component assay: conducting ultra performance liquid chromatography (UPLC) at a characteristic wavelength of the Chinese medicinal materials or herbal slices using octadecyl silane (ODS) chemically bonded silica as packing; using 0.1% formic acid-water as mobile phase A and acetonitrile as mobile phase B, conducting gradient elution according to the following conditions: volume ratio of the mobile phase B at 0-2 min: 2%; volume ratio of the mobile phase B at 2-10 min: 2% to 100%; volume ratio of the mobile phase B at 10-13 min: 100% to 2%; volume ratio of the mobile phase B at 13-20 min: 2%; volume flow: 0.2 mL/min; column temperature: 25° C.; injection volume: 2 μL.

Further, in step (2), the in vitro bioactivity assay for TCM is to detect $ABTS^+$ free radical scavenging activity (%), DPPH radical scavenging activity (%), and hydroxyl radical scavenging activity.

Still further, in step (3), the principal component assay for TCM includes principal component analysis (PCA) and hierarchical clustering analysis (HCA). Specifically, the whole process of the analytical methods includes: PCA: principal component analysis; and HCA: hierarchical cluster analysis.

Further, in step (4), the quality grade of TCM is classified into $P_{Excellent}$, $P_{Good}$, $P_{Fair}$, and $P_{Poor}$, where P is in the range of $0 \leq P \leq 1$, and the corresponding specific grade detection formulas are as follows:

$$P_{Excellent} = \frac{\exp(\beta_{Excellent} + \beta_{Excellent\ activity\ 1} X_{Excellent\ activity\ 1} + \beta_{Excellent\ activity\ 2} X_{Excellent\ activity\ 2} + \cdots \beta_{Excellent\ activity\ n} X_{Excellent\ activity\ n} + \beta_{Excellent\ component\ 1} X_{Excellent\ component\ 1} + \beta_{Excellent\ component\ 2} X_{Excellent\ component\ 2} + \cdots \beta_{Excellent\ component\ n} X_{Excellent\ component\ n})}{1 + \exp(\beta_{Excellent} + \beta_{Excellent\ activity\ 1} X_{Excellent\ activity\ 1} + \beta_{Excellent\ activity\ 2} X_{Excellent\ activity\ 2} + \cdots \beta_{Excellent\ activity\ n} X_{Excellent\ activity\ n} + \beta_{Excellent\ component\ 1} X_{Excellent\ component\ 1} + \beta_{Excellent\ component\ 2} X_{Excellent\ component\ 2} + \cdots \beta_{Excellent\ component\ n} X_{Excellent\ component\ n})}$$

$$P_{Good} = \frac{\exp(\beta_{Good} + \beta_{Good\ activity\ 1} X_{Good\ activity\ 1} + \beta_{Good\ activity\ 2} X_{Good\ activity\ 2} + \cdots \beta_{Good\ activity\ n} X_{Good\ activity\ n} + \beta_{Good\ component\ 1} X_{Good\ component\ 1} + \beta_{Good\ component\ 2} X_{Good\ component\ 2} + \cdots \beta_{Good\ component\ n} X_{Good\ component\ n})}{1 + \exp(\beta_{Good} + \beta_{Good\ activity\ 1} X_{Good\ activity\ 1} + \beta_{Good\ activity\ 2} X_{Good\ activity\ 2} + \cdots \beta_{Good\ activity\ n} X_{Good\ activity\ n} + \beta_{Good\ component\ 1} X_{Good\ component\ 1} + \beta_{Good\ component\ 2} X_{Good\ component\ 2} + \cdots \beta_{Good\ component\ n} X_{Good\ component\ n})}$$

$$P_{Fair} = \frac{\exp(\beta_{Fair} + \beta_{Fair\ activity\ 1} X_{Fair\ activity\ 1} + \beta_{Fair\ activity\ 2} X_{Fair\ activity\ 2} + \cdots \beta_{Fair\ activity\ n} X_{Fair\ activity\ n} + \beta_{Fair\ component\ 1} X_{Fair\ component\ 1} + \beta_{Fair\ component\ 2} X_{Fair\ component\ 2} + \cdots \beta_{Fair\ component\ n} X_{Fair\ component\ n})}{1 + \exp(\beta_{Fair} + \beta_{Fair\ activity\ 1} X_{Fair\ activity\ 1} + \beta_{Fair\ activity\ 2} X_{Fair\ activity\ 2} + \cdots \beta_{Fair\ activity\ n} X_{Fair\ activity\ n} + \beta_{Fair\ component\ 1} X_{Fair\ component\ 1} + \beta_{Fair\ component\ 2} X_{Fair\ component\ 2} + \cdots \beta_{Fair\ component\ n} X_{Fair\ component\ n})}$$

-continued $$P_{Poor} = \frac{\exp(\beta_{Poor} + \beta_{Poor\ activity\ 1}X_{Poor\ activity\ 1} + \beta_{Poor\ activity\ 2}X_{Poor\ activity\ 2} + \cdots \beta_{Poor\ activity\ n}X_{Poor\ activity\ n} + \beta_{Poor\ component\ 1}X_{Poor\ component\ 1} + \beta_{Poor\ component\ 2}X_{Poor\ component\ 2} + \cdots \beta_{Poor\ component\ n}X_{Poor\ component\ n})}{1 + \exp(\beta_{Poor} + \beta_{Poor\ activity\ 1}X_{Poor\ activity\ 1} + \beta_{Poor\ activity\ 2}X_{Poor\ activity\ 2} + \cdots \beta_{Poor\ activity\ n}X_{Poor\ activity\ n} + \beta_{Poor\ component\ 1}X_{Poor\ component\ 1} + \beta_{Poor\ component\ 2}X_{Poor\ component\ 2} + \cdots \beta_{Poor\ component\ n}X_{Poor\ component\ n})}$$

Still further, the TCM may be any one of Cinnamomi Ramulus, Salviae Miltiorrhizae Radix et Rhizoma or Achyranthis Bidentatae Radix. Still further, quality grade detection formulas of the Cinnamomi Ramulus are as follows:

$$P_{Excellent} = \frac{\exp\begin{pmatrix} -0.974\ Antioxidant_{DPPH} + 2.197\ Antioxidant_{OH} - \\ 0.96 C_{Cinnamaldehyde} + 10.158 C_{Cinnamic\ acid} + \\ 44.7 C_{Cinnamyl\ alcohol} - 43.222 C_{Coumarin} + 32.543 \end{pmatrix}}{1 + \exp\begin{pmatrix} -0.974\ Antioxidant_{DPPH} + 2.197\ Antioxidant_{OH} - \\ 0.96 C_{Cinnamaldehyde} + 10.158 C_{Cinnamic\ acid} + \\ 44.7 C_{Cinnamyl\ alcohol} - 43.222 C_{Coumarin} + 32.543 \end{pmatrix}}$$

$$P_{Good} = \frac{\exp\begin{pmatrix} 2.545\ Antioxidant_{DPPH} - 0.744\ Antioxidant_{OH} - \\ 0.827 C_{Cinnamaldehyde} - 35.909 C_{Cinnamic\ acid} - \\ 91.409 C_{Cinnamyl\ alcohol} + 117.883 C_{Coumarin} - 449.205 \end{pmatrix}}{1 + \exp\begin{pmatrix} 2.545\ Antioxidant_{DPPH} - 0.744\ Antioxidant_{OH} - \\ 0.827 C_{Cinnamaldehyde} - 35.909 C_{Cinnamic\ acid} - \\ 91.409 C_{Cinnamyl\ alcohol} + 117.883 C_{Coumarin} - 449.205 \end{pmatrix}}$$

$$P_{Fair} = \frac{\exp\begin{pmatrix} 1.093\ Antioxidant_{DPPH} - 1.521\ Antioxidant_{OH} + \\ 1.343 C_{Cinnamaldehyde} + 31.391 C_{Cinnamic\ acid} + \\ 22.043 C_{Cinnamyl\ alcohol} + 6.076 C_{Coumarin} - 196.728 \end{pmatrix}}{1 + \exp\begin{pmatrix} 1.093\ Antioxidant_{DPPH} - 1.521\ Antioxidant_{OH} + \\ 1.343 C_{Cinnamaldehyde} + 31.391 C_{Cinnamic\ acid} + \\ 22.043 C_{Cinnamyl\ alcohol} + 6.076 C_{Coumarin} - 196.728 \end{pmatrix}}$$

$$P_{Poor} = \frac{\exp\begin{pmatrix} -0.875\ Antioxidant_{DPPH} + 0.892\ Antioxidant_{OH} - \\ 0.952 C_{Cinnamaldehyde} - 33.664 C_{Cinnamic\ acid} - \\ 20.326 C_{Cinnamyl\ alcohol} - 9.724 C_{Coumarin} + 199.880 \end{pmatrix}}{1 + \exp\begin{pmatrix} -0.875\ Antioxidant_{DPPH} + 0.892\ Antioxidant_{OH} - \\ 0.952 C_{Cinnamaldehyde} - 33.664 C_{Cinnamic\ acid} - \\ 20.326 C_{Cinnamyl\ alcohol} - 9.724 C_{Coumarin} + 199.880 \end{pmatrix}}$$

Further, quality grade detection formulas of the Salviae Miltiorrhizae Radix et Rhizoma areas follows:

$$P_{Excellent} = \frac{\exp\begin{pmatrix} -12.692 + 1.571 C_{Tanshinone\ IIA} - 1.056 C_{Salvianolic\ acid\ B} + \\ 1.272 Anitoxidant_{DPPH} - 0.152 Antioxidant_{OH} \end{pmatrix}}{1 + \exp\begin{pmatrix} -12.692 + 1.571 C_{Tanshinone\ IIA} - \\ 1.056 C_{Salvianolic\ acid\ B} + \\ 1.272 Anitoxidant_{DPPH} - 0.152 Antioxidant_{OH} \end{pmatrix}}$$

$$P_{Good} = \frac{\exp\begin{pmatrix} 118.369 - 3.453 C_{Tanshinone\ IIA} + 0.642 C_{Salvianolic\ acid\ B} - \\ 5.175 Anitoxidant_{DPPH} + 0.645 Antioxidant_{OH} \end{pmatrix}}{1 + \exp\begin{pmatrix} 118.369 - 3.453 C_{Tanshinone\ IIA} + \\ 0.642 C_{Salvianolic\ acid\ B} - \\ 5.175 Anitoxidant_{DPPH} + 0.645 Antioxidant_{OH} \end{pmatrix}}$$

$$P_{Fair} = \frac{\exp\begin{pmatrix} 69.307 - 12.857 C_{Tanshinone\ IIA} + 1.326 C_{Salvianolic\ acid\ B} - \\ 0.771 Anitoxidant_{DPPH} - 1.160 Antioxidant_{OH} \end{pmatrix}}{1 + \exp\begin{pmatrix} 69.307 - 12.857 C_{Tanshinone\ IIA} + \\ 1.326 C_{Salvianolic\ acid\ B} - \\ 0.771 Anitoxidant_{DPPH} - 1.160 Antioxidant_{OH} \end{pmatrix}}$$

$$P_{Poor} = \frac{\exp\begin{pmatrix} -89.539 + 3.845 C_{Tanshinone\ IIA} + 1.166 C_{Salvianolic\ acid\ B} - \\ 0.240 Anitoxidant_{DPPH} + 0.119 Antioxidant_{OH} \end{pmatrix}}{1 + \exp\begin{pmatrix} -89.539 + 3.845 C_{Tanshinone\ IIA} + \\ 1.166 C_{Salvianolic\ acid\ B} - \\ 0.240 Anitoxidant_{DPPH} + 0.119 Antioxidant_{OH} \end{pmatrix}}$$

Further, quality grade detection formulas of the Achyranthis Bidentatae Radix are as follows:

$$P_{Excellent} = \frac{\exp(-31.020 + 0.146 Antioxidant_{DPPH} + 0.098 Antioxidant_{OH} + 222.140 C_{Ecdysone})}{1 + \exp(-31.020 + 0.146 Antioxidant_{DPPH} + 0.098 Antioxidant_{OH} + 222.140 C_{Ecdysone})}$$

$$P_{Good} = \frac{\exp(-5.713 + 0.068 Antioxidant_{DPPH} + 0.023 Antioxidant_{OH} + 17.3560 C_{Ecdysone})}{1 + \exp(-5.713 + 0.068 Antioxidant_{DPPH} + 0.023 Antioxidant_{OH} + 17.3560 C_{Ecdysone})}$$

$$P_{Fair} = \frac{\exp(5.962 - 0.058 Antioxidant_{DPPH} - 0.006 Antioxidant_{OH} - 49.559 C_{Ecdysone})}{1 + \exp(5.962 - 0.058 Antioxidant_{DPPH} - 0.006 Antioxidant_{OH} - 49.559 C_{Ecdysone})}$$

$$P_{Poor} = \frac{\exp(615.117 - 15.432 Antioxidant_{DPPH} + 6.252 Antioxidant_{OH} - 11574.00 C_{Ecdysone})}{1 + \exp(615.117 - 15.432 Antioxidant_{DPPH} + 6.252 Antioxidant_{OH} - 11574.00 C_{Ecdysone})}$$

In the technical solution of the present invention, in vitro activity assay for TCM and PCA are completed by exploratory analysis, and specific experimental exploration methods include as follows:

(1) In Vitro Assay:

1) Detection of ABTS$^+$ Free Radical Scavenging Activity

An ABTS working solution and an enzyme working solution are prepared with reference to a rapid ABTS method. Each run of total antioxidant capacity (T-AOC) is detected. The ABTS$^+$ free radical scavenging activity is calculated according to the following expression:

$$ABTS^+ \text{ free radical scavenging activity } (\%) = \frac{A_0 - A_i}{A_0} \times 100\%$$

where, $A_0$ is absorbance of ABTS$^+$ free radical without sample; $A_i$ is absorbance of ABTS$^+$ free radical after reaction with a sample.

2) Detection of Hydroxyl Radical Scavenging Activity

With reference to a detection method for hydroxyl radical scavenging activity, an application solution and a chromogenic reagent are prepared, respectively; the application solution is pre-incubated in water bath for 3 min at 37° C.; sample solution is diluted with distilled water to different concentrations of test solutions; each run of hydroxyl radical scavenging activity is detected with different concentrations of test solutions. The hydroxyl radical scavenging activity is calculated according to the following expression:

$$\text{Hydroxyl radical scavenging activity (U/mL)} = \frac{OD_{Reference} - OD_{Sample}}{OD_{Standard} - OD_{Blank}} \times$$

$$8.824 \frac{mmol}{L} \times \frac{1 \text{ mL}}{0.2 \text{ mL}} \times \text{Dilution multiple before sample testing}$$

3) Detection of DPPH Radical Scavenging Activity

A DPPH working solution and an enzyme working solution are prepared with reference to a detection method for DPPH radical scavenging activity. Each run of DPPH radical scavenging activity is detected. The DPPH radical scavenging activity is calculated according to the following expression:

$$\text{DPPH radical scavenging activity (\%)} = \frac{A_0 - A_i}{A_0} \times 100\%$$

where, $A_0$ is absorbance of DPPH free radical without sample; $A_i$ is absorbance of DPPH free radical after reaction with a sample.

(2) PCA:

In order to evaluate how the model classifies samples more intuitively, sample data for each training set are subjected to dimension reduction, and sample differences are observed by PCA. After data alignment, integration, and standardization, the chromatographically detected fingerprint data (n≥6) are imported into multivariate statistical software, and PCA is conducted with influencing factors as observed values (X). Principal components with the most differential variables are extracted from the resulting data matrix. Eigenvalues and cumulative contribution are obtained from a correlation coefficient matrix R. Model fitting degree obtained by extracting the first two principal components should be >80%. Selecting the first two principal components for model prediction can reflect basic characteristics of different grades of herbal slices fed. The first two principal components are projected to obtain a scatter diagram. Respective run of data are analyzed by hierarchical clustering analysis (HCA), and sample classification is observed, as shown in FIG. 1. Chemical indexes with high contribution of sample difference are preliminarily judged from a components load diagram, and components thereof are identified, as shown in FIG. 2. Samples are detected by liquid chromatography, and content of each identified chemical component is calculated by the external standard method.

(3) Establishment of Binary Logistic Regression Model:

Based on the established principal component logistic regression model, application effect is fully dependent on the accuracy of the grade classification standard for quality-influencing factors.

The logistic model is used to establish a functional relationship between principal components corresponding to samples of each training set and grade. Parameters of the logistic model are solved by SPSS software to obtain the following model expressions:

$$P_{Excellent} = \frac{\exp\begin{pmatrix} \beta_{Excellent} + \beta_{Excellent\ activity\ 1} X_{Excellent\ activity\ 1} + \\ \beta_{Excellent\ activity\ 2} X_{Excellent\ activity\ 2} + \cdots \\ \beta_{Excellent\ activity\ n} X_{Excellent\ activity\ n} + \\ \beta_{Excellent\ component\ 1} X_{Excellent\ component\ 1} + \\ \beta_{Excellent\ component\ 2} X_{Excellent\ component\ 2} + \cdots \\ \beta_{Excellent\ component\ n} X_{Excellent\ component\ n} \end{pmatrix}}{1 + \exp\begin{pmatrix} \beta_{Excellent} + \beta_{Excellent\ activity\ 1} X_{Excellent\ activity\ 1} + \\ \beta_{Excellent\ activity\ 2} X_{Excellent\ activity\ 2} + \cdots \\ \beta_{Excellent\ activity\ n} X_{Excellent\ activity\ n} + \\ \beta_{Excellent\ component\ 1} X_{Excellent\ component\ 1} + \\ \beta_{Excellent\ component\ 2} X_{Excellent\ component\ 2} + \cdots \\ \beta_{Excellent\ component\ n} X_{Excellent\ component\ n} \end{pmatrix}}$$

$$P_{Good} = \frac{\exp\begin{pmatrix} \beta_{Good} + \beta_{Good\ activity\ 1} X_{Good\ activity\ 1} + \\ \beta_{Good\ activity\ 2} X_{Good\ activity\ 2} + \cdots \\ \beta_{Good\ activity\ n} X_{Good\ activity\ n} + \\ \beta_{Good\ component\ 1} X_{Good\ component\ 1} + \\ \beta_{Good\ component\ 2} X_{Good\ component\ 2} + \cdots \\ \beta_{Good\ component\ n} X_{Good\ component\ n} \end{pmatrix}}{1 + \exp\begin{pmatrix} \beta_{Good} + \beta_{Good\ activity\ 1} X_{Good\ activity\ 1} + \\ \beta_{Good\ activity\ 2} X_{Good\ activity\ 2} + \cdots \\ \beta_{Good\ activity\ n} X_{Good\ activity\ n} + \\ \beta_{Good\ component\ 1} X_{Good\ component\ 1} + \\ \beta_{Good\ component\ 2} X_{Good\ component\ 2} + \cdots \\ \beta_{Good\ component\ n} X_{Good\ component\ n} \end{pmatrix}}$$

$$P_{Fair} = \frac{\exp\begin{pmatrix} \beta_{Fair} + \beta_{Fair\ activity\ 1} X_{Fair\ activity\ 1} + \\ \beta_{Fair\ activity\ 2} X_{Fair\ activity\ 2} + \cdots \\ \beta_{Fair\ activity\ n} X_{Fair\ activity\ n} + \\ \beta_{Fair\ component\ 1} X_{Fair\ component\ 1} + \\ \beta_{Fair\ component\ 2} X_{Fair\ component\ 2} + \cdots \\ \beta_{Fair\ component\ n} X_{Fair\ component\ n} \end{pmatrix}}{1 + \exp\begin{pmatrix} \beta_{Fair} + \beta_{Fair\ activity\ 1} X_{Fair\ activity\ 1} + \\ \beta_{Fair\ activity\ 2} X_{Fair\ activity\ 2} + \cdots \\ \beta_{Fair\ activity\ n} X_{Fair\ activity\ n} + \\ \beta_{Fair\ component\ 1} X_{Fair\ component\ 1} + \\ \beta_{Fair\ component\ 2} X_{Fair\ component\ 2} + \cdots \\ \beta_{Fair\ component\ n} X_{Fair\ component\ n} \end{pmatrix}}$$

$$P_{Poor} = \frac{\exp\begin{pmatrix} \beta_{Poor} + \beta_{Fair\ activity\ 1} X_{Poor\ activity\ 1} + \\ \beta_{Poor\ activity\ 2} X_{Poor\ activity\ 2} + \cdots \\ \beta_{Poor\ activity\ n} X_{Poor\ activity\ n} + \\ \beta_{Poor\ component\ 1} X_{Poor\ component\ 1} + \\ \beta_{Poor\ component\ 2} X_{Poor\ component\ 2} + \cdots \\ \beta_{Poor\ component\ n} X_{Poor\ component\ n} \end{pmatrix}}{1 + \exp\begin{pmatrix} \beta_{Poor} + \beta_{Fair\ activity\ 1} X_{Poor\ activity\ 1} + \\ \beta_{Poor\ activity\ 2} X_{Poor\ activity\ 2} + \cdots \\ \beta_{Poor\ activity\ n} X_{Poor\ activity\ n} + \\ \beta_{Poor\ component\ 1} X_{Poor\ component\ 1} + \\ \beta_{Poor\ component\ 2} X_{Poor\ component\ 2} + \cdots \\ \beta_{Poor\ component\ n} X_{Poor\ component\ n} \end{pmatrix}}$$

Measured value of each index in a test set is substituted in the above expressions in sequence to calculate a probability of which grade an influencing factor belongs to, thereby determining the grade of Chinese medicinal materials/herbal slices. If a result is calculated to be close to 1, the corresponding grade will be judged.

The present invention has the following beneficial effects:
1. The present invention establishes a grade detection method of TCM, where training samples are merely required to described as "yes" or "no" by binary logistic regression and results are allowed to obtain precise scores, ensuring the objectivity of grading results; meanwhile, binary logistic regression takes into account the interactions of a plurality of influencing factors during TCM production comprehensively, and enables comprehensive and practical evaluation results; further, statistical methods may be used to test the degree of importance of each detection index in the training set data in classification accuracy to rule out secondary indexes.

2. Based on a research method for "component-efficacy" interaction, the technology of the present invention introduces the concept of integrative omics into quality evaluation of TCM. This coincides with the concept of "holistic view" of quality control and evaluation of TCM, and reflects the idea of quality control of TCM, i.e., "components reflect the activity and activity points to the efficacy".

3. The method for grade evaluation of TCM established by the present invention and the established mathematical model method for predicting Chinese medicinal materials or herbal slices provides a better scientific data support for evaluating grades and specifications for TCM commodities; also, the method satisfies transaction demands for "fixing prices according to quality of TCM" during circulation, and ensure the safety and effectiveness of clinical medication of TCM.

DETAILED DESCRIPTION

Figure 1:
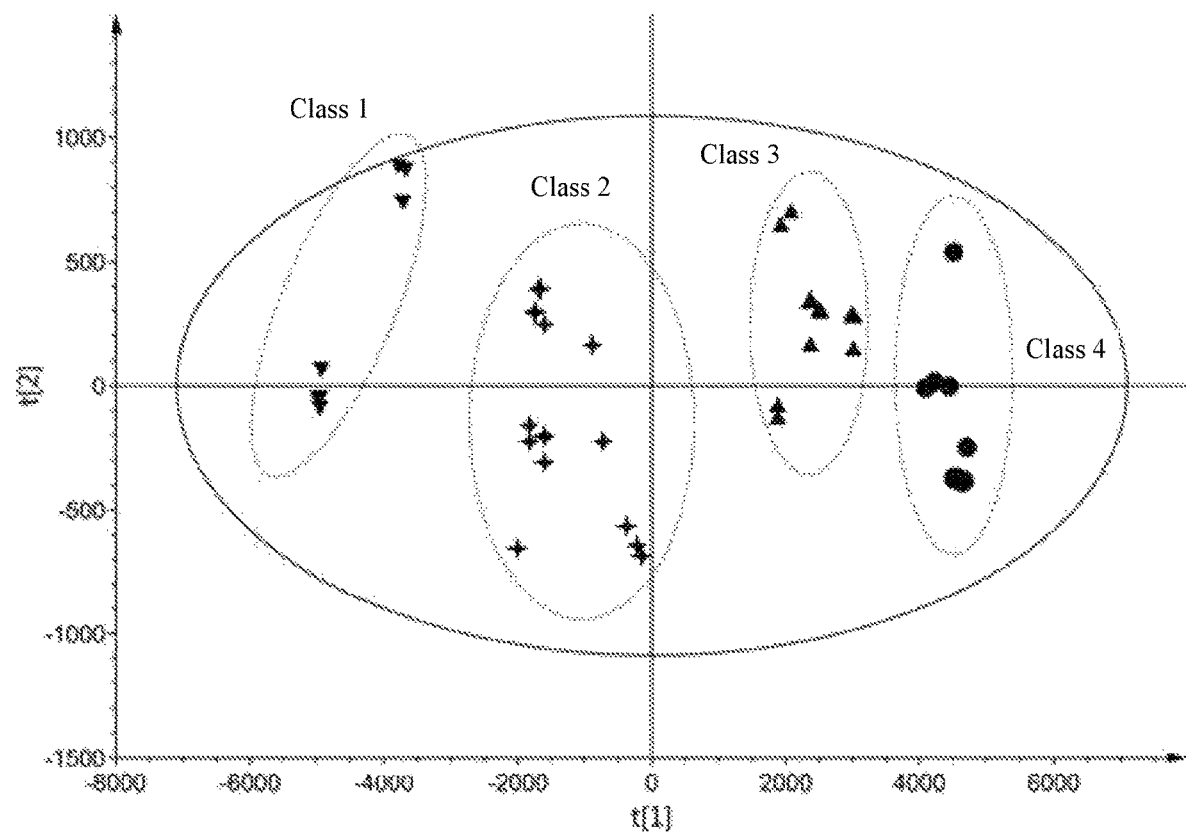
FIG. 1 is a scatter diagram of principal component classification of TCM in the solution of the present invention.
Figure 2:
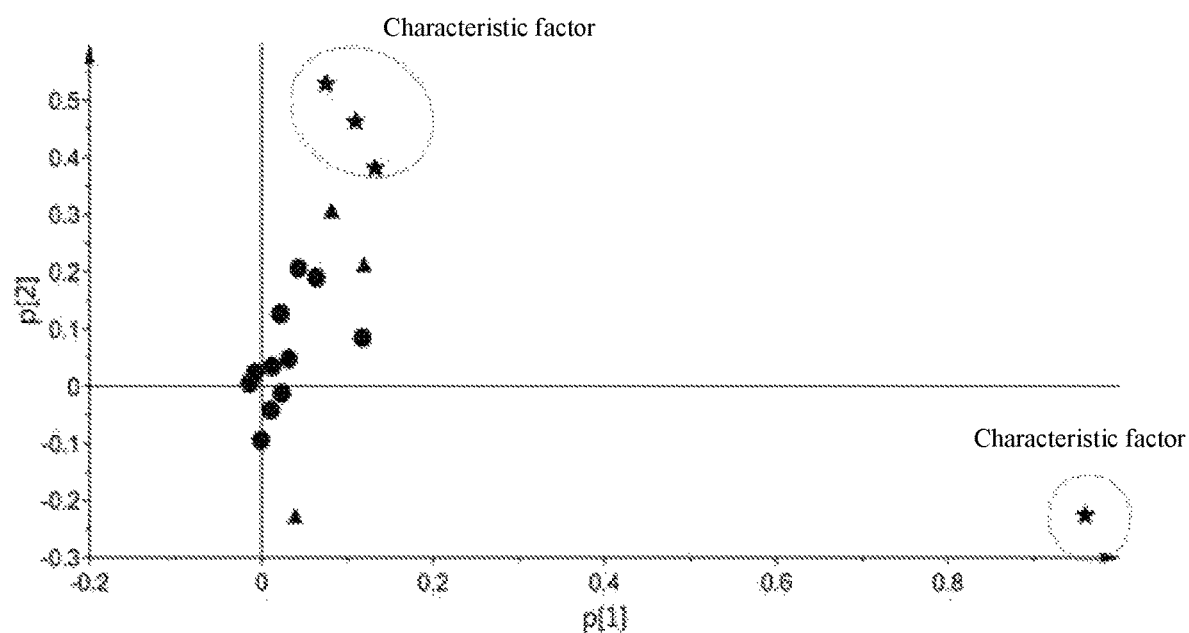
FIG. 2 is a load diagram of principal component analysis of TCM in the solution of the present invention.

To make the objectives, technical solutions, and advantages of the present invention clearer, the following further describes the present invention in detail with reference to the accompanying drawings and examples. It should be understood that the examples described herein are merely used to explain the present invention, rather than to limit the present invention.

Example 1 Detection Method for Quality Grade of Cinnamomi Ramulus (1) Sample preparation: Approximately 0.3 g of Cinnamomi Ramulus powder (passed through #4 sieve) was weighed accurately in a conical flask with cover, mixed with 50 mL of methanol accurately, sealed tightly, weighed, sonicated (power 140 W, frequency 42 kHz) for 30 min, cooled, and weighed again; methanol was used to make up for a weight loss; the mixture was shaken well and filtered to collect a subsequent filtrate as a sample solution.

(2) Acquisition of integral data for a fingerprint of Cinnamomi Ramulus by ultra performance liquid chromatography (UPLC): Using octadecyl silane (ODS) chemically bonded silica as packing, UPLC was conducted at a characteristic wavelength (254 nm) of principal components of Cinnamomi Ramulus; using 0.1% formic acid-water as mobile phase A and acetonitrile as mobile phase B, gradient elution was conducted according to the following conditions: volume ratio of the mobile phase B at 0-2 min: 2%; volume ratio of the mobile phase B at 2-10 min: 2% to 100%; volume ratio of the mobile phase B at 10-13 min: 100% to 2%; volume ratio of the mobile phase B at 13-20 min: 2%; volume flow: 0.2 mL/min; column temperature: 25° C.; injection volume: 2 µL. Chromatographic integration data were acquired.

(3) Assay for in vitro antioxidant indexes: Results of $Antioxidant_{ABTS+}$, $Antioxidant_{DPPH}$, and $Antioxidant_{OH}$ are listed in Table 1:

TABLE 1

Results of in vitro antioxidant indexes of Cinnamomi Ramulus

| No. | Place of origin | $ABTS^+$ free radical scavenging activity (%) | DPPH radical scavenging activity (%) | Hydroxyl radical scavenging activity (U/mL) |
|---|---|---|---|---|
| S1 | Cenxi City, Guangxi (Excellent) | 10.61 | 64.47 | 87.09 |
| S2 | Cenxi City, Guangxi (Good) | 10.26 | 20.82 | 36.09 |
| S3 | Cenxi City, Guangxi (Fair) | 10.85 | 90.63 | 28.31 |
| S4 | Cenxi City, Guangxi (Poor) | 9.25 | 59.61 | 51.43 |
| S5 | Heyuan County, Guangdong (tender Cinnamomi Ramulus) | 12.16 | 61.40 | 65.48 |
| S6 | Guiping City, Guangxi (tender Cinnamomi Ramulus) | 10.66 | 84.98 | 94.17 |
| S7 | Heyuan County, Guangdong (tender Cinnamomi Ramulus) | 12.64 | 62.16 | 56.88 |
| S8 | Yulin City, Guangxi (tender Cinnamomi Ramulus) | 8.98 | 70.95 | 80.09 |
| S9 | Lecheng Town, Guangdong | 8.57 | 90.53 | 70.16 |
| S10 | Binheng Town, Guangdong | 10.57 | 84.98 | 94.17 |
| S11 | Daquan Town, Guangxi | 13.13 | 59.73 | 8.65 |
| S12 | Yunan County, Guangxi | 23.78 | 70.29 | 16.31 |
| S13 | Wuhe Town, Guangdong | 9.74 | 57.14 | 95.10 |
| S14 | Tongting Town, Guangxi | 10.47 | 55.14 | 85.10 |
| S15 | Zhongsha Town, Guangxi | 9.12 | 49.41 | 23.94 |
| S16 | Zhongsha Town, Guangxi | 10.63 | 69.64 | 45.57 |
| S17 | Tongting Town, Guangxi | 19.01 | 72.99 | 58.71 |
| S18 | Yulin City, Guangxi (inferior) | 20.48 | 60.77 | 14.36 |
| S19 | Shaanxi Xingshengde Pharmaceutical Co., Ltd. | 11.60 | 79.51 | 82.96 |
| S20 | Shaanxi Buchang Pharmaceutical Co., Ltd. | 13.84 | 38.42 | 48.02 |

(4) Principal Component Analysis (PCA):

After data alignment, integration, and standardization, the acquired data (n=6) were imported into Simca-p 14.1 software, and PCA was conducted with integral data and bioactivity data as observed values (X). Principal components with the most differential variables were extracted from the resulting data matrix. Eigenvalues and cumulative contribution were obtained from a correlation coefficient matrix R. A model fitted two principal components automatically. Model fitting degree was 95.9%. Contribution of principal component 1 (PC1) was 95.9%, with the most difference information, suggestive of a good fitting ability of the model. The first two principal components were projected, and respective run of data were analyzed by hierarchical clustering analysis (HCA). After preliminary judgment from components load results, chemical indexes with high contribution of sample difference included cinnamaldehyde, cinnamyl alcohol, cinnamic acid, and coumarin; in vitro activity indexes included DPPH radical scavenging activity (Antioxidant$_{DPPH}$) and hydroxyl radical scavenging activity (Antioxidant$_{OH}$). Appropriate amounts of reference substances (RS) of cinnamaldehyde, cinnamyl alcohol, cinnamic acid, and coumarin (principal components in Cinnamomi Ramulus) were weighed accurately in a brown volumetric flask, and prepared into a 0.5 mg/mL (mass concentration) solution with methanol; the solution was filtered through a 0.22 μm filter membrane to collect a subsequent filtrate as a reference solution. Content of each identified chemical component was calculated by external standard method of liquid chromatography. Variables were set as: $C_{Cinnamaldehyde}$, $C_{Cinnamyl\ alcohol}$, $C_{Cinnamic\ acid}$, $C_{Coumarin}$, Antioxidant$_{DPPH}$, and Antioxidant$_{OH}$.

(5) Functional relationship among chemical component content, antioxidant activity, and experience level corresponding to samples of each training set was established by a binary logistic model:

Model expressions are obtained as follows $$P_{Excellent} = \frac{\exp\begin{pmatrix} -0.974\ Antioxidant_{DPPH} + 2.197\ Antioxidant_{OH} - \\ 0.96 C_{Cinnamaldehyde} + 10.158 C_{Cinnamic\ acid} + \\ 44.7 C_{Cinnamyl\ alcohol} - 43.222 C_{Coumarin} + 32.543 \end{pmatrix}}{1 + \exp\begin{pmatrix} -0.974\ Antioxidant_{DPPH} + 2.197\ Antioxidant_{OH} - \\ 0.96 C_{Cinnamaldehyde} + 10.158 C_{Cinnamic\ acid} + \\ 44.7 C_{Cinnamyl\ alcohol} - 43.222 C_{Coumarin} + 32.543 \end{pmatrix}}$$

$$P_{Good} = \frac{\exp\begin{pmatrix} 2.545\ Antioxidant_{DPPH} - 0.744\ Antioxidant_{OH} - \\ 0.827 C_{Cinnamaldehyde} - 35.909 C_{Cinnamic\ acid} - \\ 91.409 C_{Cinnamyl\ alcohol} + 117.883 C_{Coumarin} - 449.205 \end{pmatrix}}{1 + \exp\begin{pmatrix} 2.545\ Antioxidant_{DPPH} - 0.744\ Antioxidant_{OH} - \\ 0.827 C_{Cinnamaldehyde} - 35.909 C_{Cinnamic\ acid} - \\ 91.409 C_{Cinnamyl\ alcohol} + 117.883 C_{Coumarin} - 449.205 \end{pmatrix}}$$

$$P_{Fair} = \frac{\exp\begin{pmatrix} 1.093\ Antioxidant_{DPPH} - 1.521\ Antioxidant_{OH} + \\ 1.343 C_{Cinnamaldehyde} + 31.391 C_{Cinnamic\ acid} + \\ 22.043 C_{Cinnamyl\ alcohol} + 6.076 C_{Coumarin} - 196.728 \end{pmatrix}}{1 + \exp\begin{pmatrix} 1.093\ Antioxidant_{DPPH} - 1.521\ Antioxidant_{OH} + \\ 1.343 C_{Cinnamaldehyde} + 31.391 C_{Cinnamic\ acid} + \\ 22.043 C_{Cinnamyl\ alcohol} + 6.076 C_{Coumarin} - 196.728 \end{pmatrix}}$$

$$P_{Poor} = \frac{\exp\begin{pmatrix} -0.875\ Antioxidant_{DPPH} + 0.892\ Antioxidant_{OH} - \\ 0.952 C_{Cinnamaldehyde} - 33.664 C_{Cinnamic\ acid} - \\ 20.326 C_{Cinnamyl\ alcohol} - 9.724 C_{Coumarin} + 199.880 \end{pmatrix}}{1 + \exp\begin{pmatrix} -0.875\ Antioxidant_{DPPH} + 0.892\ Antioxidant_{OH} - \\ 0.952 C_{Cinnamaldehyde} - 33.664 C_{Cinnamic\ acid} - \\ 20.326 C_{Cinnamyl\ alcohol} - 9.724 C_{Coumarin} + 199.880 \end{pmatrix}}$$

Measured value of each index was substituted in the above expressions to calculate a probability of which grade an influencing factor belongs to, thereby determining the grade of Cinnamomi Ramulus. Detailed grade calculation results of 20 batches of Cinnamomi Ramulus are listed in Table 2, and probabilities thereof are determined as >95%.

TABLE 2

Grade classification results of *Cinnamomi Ramulus*

| Grade | Source | Probability |
|---|---|---|
| 4 | Wuhe Town, Guangdong/Ungraded | 1.00 |
| 4 | Binheng Town, Guangdong/Ungraded | 1.00 |
| 4 | Cenxi City, Guangxi/Superior | 1.00 |
| 3 | Yulin City, Guangxi/Ungraded | 1.00 |
| 3 | Heyuan County, Guangdong/Small | 1.00 |
| 3 | Shaanxi Xingshengde Pharmaceutical Co., Ltd./Ungraded | 1.00 |
| 3 | Cenxi City, Guangxi/Fair | 1.00 |
| 2 | Lecheng Town, Guangdong/Large | 0.99 |
| 2 | Heyuan County, Guangdong/Ungraded | 0.99 |
| 2 | Cenxi City, Guangxi/Good | 1.00 |
| 2 | Zhongsha Town, Guangxi/Ungraded | 0.97 |
| 2 | Yulin City, Guangxi/Inferior | 1.00 |
| 2 | Daquan Town, Guangxi/Ungraded | 1.00 |
| 1 | Tongting Town, Guangxi/Small | 1.00 |
| 1 | Tongting Town, Guangxi/Ungraded | 1.00 |
| 1 | Guiping City, Guangxi/Ungraded | 1.00 |
| 1 | Cenxi City, Guangxi/Poor | 1.00 |
| 1 | Shaanxi Buchang Pharmaceutical Co., Ltd./Ungraded | 1.00 |
| 1 | Zhongsha Town, Guangxi/Ungraded | 1.00 |
| 1 | Yunan County, Guangxi/Ungraded | 1.00 |

Example 2 Detection Method for Quality Grade of Salviae Miltiorrhizae Radix Et Rhizoma (1) Sample preparation: Approximately 0.3 g of Salviae Miltiorrhizae Radix et Rhizoma powder (passed through #4 sieve) was weighed accurately in a conical flask with cover, mixed with 50 mL of methanol accurately, sealed tightly weighed, sonicated (power 140 W, frequency 42 kHz) for 30 min, cooled, and weighed again; methanol was used to make up for a weight loss; the mixture was shaken well and filtered to collect a subsequent filtrate as a sample solution.

(2) Acquisition of integral data for a fingerprint of Salviae Miltiorrhizae Radix et Rhizoma by ultra performance liquid chromatography (UPLC): Using octadecyl silane (ODS) chemically bonded silica as packing, UPLC was conducted at a characteristic wavelength (270 nm) of principal components of Salviae Miltiorrhizae Radix et Rhizoma; using 0.1% formic acid-water as mobile phase A and acetonitrile as mobile phase B, gradient elution was conducted according to the following conditions: volume ratio of the mobile phase B at 0-2 min: 2%; volume ratio of the mobile phase B at 2-10 min: 2% to 100%; volume ratio of the mobile phase B at 10-13 min: 100% to 2%; volume ratio of the mobile phase B at 13-20 min: 2%; volume flow: 0.2 mL/min; column temperature: 25° C.; injection volume: 2 μL. Chromatographic integration data were acquired.

(3) Assay for in vitro antioxidant indexes: Results of $Antioxidant_{ABTS+}$, $Antioxidant_{DPPH}$, and $Antioxidant_{OH}$ are listed in Table 3.

(4) Principal component analysis (PCA): Chromatographic integration data and antioxidant data were imported into multivariate statistical software for PCA. After data alignment, integration, and standardization, the acquired data (n=6) were imported into Simca-p 14.1 software, and PCA was conducted with integral data and bioactivity data as observed values (X). Principal components with the most differential variables were extracted from the resulting data matrix. Eigenvalues and cumulative contribution were obtained from a correlation coefficient matrix R. A model fitted two principal components automatically. Model fitting degree was 83.90%. Contribution of principal component 1 (PC1) was 66.1%, with the most difference information, suggestive of a good fitting ability of the model. The first two principal components were projected, and respective run of data were analyzed by hierarchical clustering analysis (HCA). After preliminary judgment from components load results, chemical indexes with high contribution of sample difference included tanshinone IIA and salvianolic acid B: in vitro activity indexes included DPPH radical scavenging activity ($Antioxidant_{DPPH}$) and hydroxyl radical scavenging activity ($Antioxidant_{OH}$). Appropriate amounts of reference substances (RS) of tanshinone IIA and salvianolic acid B (principal components in Salviae Miltiorrhizae Radix et Rhizoma) were weighed accurately in a brown volumetric flask, and prepared into 0.21 mg/mL and 0.22 mg/mL (mass concentration) solutions with methanol, respectively; the solutions were filtered through a 0.22 μm filter membrane to collect subsequent filtrates as reference solutions. Content of each identified chemical component was calculated by external standard method of liquid chromatography. Variables were set as: $C_{Salvianolic\ acid\ B}$, $C_{Tanshinone\ IIA}$, $Antioxidant_{DPPH}$, and $Antioxidant_{OH}$.

TABLE 3

Results of in vitro antioxidant indexes of *Salviae Miltiorrhizae* Radix et Rhizoma

| Batch | Place of origin | $ABTS^+$ free radical scavenging activity (%) | DPPH radical scavenging activity (%) | Hydroxyl radical scavenging activity (U/mL) |
|---|---|---|---|---|
| S1 | Fangcheng County, Henan | 34.01 | 42.77 | 64.79 |
| S2 | Qingdao City, Shandong (Fair) | 20.25 | 29.81 | 46.06 |
| S3 | Yantai City, Shandong | 38.02 | 59.40 | 73.63 |
| S4 | Tai'an City, Shandong | 34.25 | 42.49 | 53.71 |
| S5 | Zhenping County, Henan | 36.75 | 54.17 | 66.93 |
| S6 | Zaozhuang City, Shandong | 25.50 | 36.49 | 73.63 |
| S7 | Zibo City, Shandong | 19.01 | 32.53 | 39.64 |
| S8 | Qingdao City, Shandong (Excellent) | 20.75 | 53.32 | 55.90 |
| S9 | Mianchi County, Henan | 34.75 | 50.50 | 68.32 |
| S10 | Shaanxi Xingshengde Pharmaceutical Co., Ltd. | 36.50 | 43.24 | 63.48 |
| S11 | Shaanxi Buchang Pharmaceutical Co., Ltd. | 39.25 | 56.72 | 76.50 |
| S12 | Wanrong County, Shanxi | 21.25 | 34.24 | 53.55 |
| S13 | Xincai County, Henan (Excellent) | 30.00 | 32.08 | 58.15 |
| S14 | Zhongjiang County, Sichuan (Excellent) | 26.75 | 38.04 | 76.91 |
| S15 | Zhongjiang County, Sichuan (Poor) | 19.10 | 30.27 | 26.84 |
| S16 | Danfeng County, Shangluo City | 30.75 | 50.18 | 52.51 |
| S17 | Luonan County, Shangluo City | 33.75 | 45.79 | 66.95 |
| S18 | Longkou Town, Henan | 30.75 | 31.48 | 62.83 |
| S19 | Hanji Town, Henan | 33.75 | 50.28 | 73.94 |
| S20 | Zhongjiang County, Sichuan (Good) | 27.00 | 42.57 | 49.91 |
| S21 | Zhongjiang County, Sichuan (Fair) | 21.25 | 32.97 | 63.96 |
| S22 | Zhongjiang County, Sichuan (Inferior) | 38.50 | 48.41 | 51.74 |
| S23 | Huangshan County, Wannan City, Anhui | 22.50 | 37.40 | 60.57 |
| S24 | Linyi City, Shandong | 26.25 | 48.15 | 73.81 |
| S25 | Shaoguan City, Guangdong | 20.50 | 45.25 | 69.74 |
| S26 | Jinan City, Shandong (Unassorted) | 31.00 | 49.84 | 62.19 |
| S27 | Jinan City, Shandong (First Grade) | 36.75 | 55.88 | 79.95 |
| S28 | Jinan City, Shandong (Second Grade) | 29.75 | 54.67 | 73.11 |
| S29 | Lijiang City, Yunnan | 20.75 | 36.55 | 36.23 |
| S30 | Counterfeit | 16.00 | 35.37 | 53.15 |
| S31 | National Institutes for Food and Drug Control, China | 29.75 | 31.72 | 68.70 |

(5) Functional relationship among chemical component content, antioxidant activity, and experience level corresponding to samples of each training set was established by a binary logistic model. Model expressions are obtained as follows:

grade of Salviae Miltiorrhizae Radix et Rhizoma. Detailed results are listed in Table 4, and probabilities thereof are determined as >87%.

TABLE 4

Grade classification results of *Salviae Miltiorrhizae* Radix el Rhizoma

| Grade | Place of origin/Original grade | Probability |
|---|---|---|
| 4 | Shaanxi Buchang Pharmaceutical Co., Ltd. | 0.99 |
| 4 | Zhenping County, Henan | 0.99 |
| 4 | Yantai City, Shandong | 0.99 |
| 4 | Danfeng County, Shangluo City | 0.99 |
| 4 | Luonan County, Shangluo City | 1.00 |
| 4 | Shaanxi Xingshengde Pharmaceutical Co., Ltd. | 0.99 |
| 3 | Zhongjiang County, Sichuan (Good) | 0.99 |
| 3 | Mianchi County, Henan | 0.91 |
| 3 | Tai'an City, Shandong | 0.99 |
| 3 | Mianchi County, Henan | 0.99 |
| 3 | Zhongjiang County, Sichuan (Inferior) | 0.99 |
| 3 | Hanji Town, Henan | 0.99 |
| 2 | Zhongjiang County, Sichuan (Fair) | 1.00 |
| 2 | Zibo City, Shandong | 0.99 |
| 2 | Qingdao City, Shandong (Fair) | 0.99 |
| 2 | Wanrong County, Shanxi | 0.93 |
| 2 | Zaozhuang City, Shandong | 0.87 |
| 2 | Xincai County, Henan (Excellent) | 0.99 |
| 2 | Longkou Town, Henan | 1.00 |
| 2 | National Institutes for Food and Drug Control, China | 0.99 |
| 2 | Zhongjiang County, Sichuan (Excellent) | 0.99 |
| 1 | Linyi City, Shandong | 0.99 |
| 1 | Shaoguan City, Guangdong | 1.00 |
| 1 | Lijiang City, Yunnan | 1.00 |
| 1 | Counterfeit | 0.99 |
| 1 | Zhongjiang County, Sichuan (Poor) | 0.99 |
| 1 | Qingdao City, Shandong (Excellent) | 0.99 |
| 1 | Jinan City, Shandong (First Grade) | 1.00 |
| 1 | Jinan City, Shandong (Second Grade) | 1.00 |
| 1 | Huangshan County, Wannan City, Anhui | 0.99 |
| 1 | Jinan City, Shandong (Unassorted) | 0.99 |

$$P_{Excellent} = \frac{\exp\left(\begin{array}{c}-12.692 + 1.571 C_{Tanshinone\ IIA} - 1.056 C_{Salvianolic\ acid\ B} + \\ 1.272 Anitoxidant_{DPPH} - 0.152 Antioxidant_{OH}\end{array}\right)}{1 + \exp\left(\begin{array}{c}-12.692 + 1.571 C_{Tanshinone\ IIA} - \\ 1.056 C_{Salvianolic\ acid\ B} + \\ 1.272 Anitoxidant_{DPPH} - 0.152 Antioxidant_{OH}\end{array}\right)}$$

$$P_{Good} = \frac{\exp\left(\begin{array}{c}118.369 - 3.453 C_{Tanshinone\ IIA} + 0.642 C_{Salvianolic\ acid\ B} - \\ 5.175 Anitoxidant_{DPPH} + 0.645 Antioxidant_{OH}\end{array}\right)}{1 + \exp\left(\begin{array}{c}118.369 - 3.453 C_{Tanshinone\ IIA} + \\ 0.642 C_{Salvianolic\ acid\ B} - \\ 5.175 Anitoxidant_{DPPH} + 0.645 Antioxidant_{OH}\end{array}\right)}$$

$$P_{Fair} = \frac{\exp\left(\begin{array}{c}69.307 - 12.857 C_{Tanshinone\ IIA} + 1.326 C_{Salvianolic\ acid\ B} - \\ 0.771 Anitoxidant_{DPPH} - 1.160 Antioxidant_{OH}\end{array}\right)}{1 + \exp\left(\begin{array}{c}69.307 - 12.857 C_{Tanshinone\ IIA} + \\ 1.326 C_{Salvianolic\ acid\ B} - \\ 0.771 Anitoxidant_{DPPH} - 1.160 Antioxidant_{OH}\end{array}\right)}$$

$$P_{Poor} = \frac{\exp\left(\begin{array}{c}-89.539 + 3.845 C_{Tanshinone\ IIA} + 1.166 C_{Salvianolic\ acid\ B} - \\ 0.240 Anitoxidant_{DPPH} + 0.119 Antioxidant_{OH}\end{array}\right)}{1 + \exp\left(\begin{array}{c}-89.539 + 3.845 C_{Tanshinone\ IIA} + \\ 1.166 C_{Salvianolic\ acid\ B} - \\ 0.240 Anitoxidant_{DPPH} + 0.119 Antioxidant_{OH}\end{array}\right)}$$

Measured value of each index was substituted in the above expressions to calculate a probability of which grade an influencing factor belongs to, thereby determining the Example 3 Detection Method for Quality Grade of Achyranthis Bidentatae Radix (1) Sample preparation: Approximately 0.3 g of Achyranthis Bidentatae Radix powder (passed through #4 sieve) was weighed accurately in a conical flask with cover, mixed with 50 mL of methanol accurately, sealed tightly, weighed, sonicated (power 140 W, frequency 42 kHz) for 30 min, cooled, and weighed again; methanol was used to make up for a weight loss; the mixture was shaken well and filtered to collect a subsequent filtrate as a sample solution.

(2) Acquisition of integral data for a fingerprint of Achyranthis Bidentatae Radix by ultra performance liquid chromatography (UPLC): Using octadecyl silane (ODS) chemically bonded silica as packing, UPLC was conducted at a characteristic wavelength (250 nm) of principal components of Achyranthis Bidentatae Radix; using 0.1% formic acid-water as mobile phase A and acetonitrile as mobile phase B, gradient elution was conducted according to the following conditions: volume ratio of the mobile phase B at 0-2 min: 2%; volume ratio of the mobile phase B at 2-10 min: 2% to 100%; volume ratio of the mobile phase B at 10-13 min: 100% to 2%; volume ratio of the mobile phase B at 13-20 min: 2%; volume flow: 0.2 mL/min; column temperature: 25° C.; injection volume: 2 μL. Chromatographic integration data were acquired.

(3) Assay for in vitro antioxidant indexes: Results of Antioxidant$_{ABTS+}$, Antioxidant$_{DPPH}$, and Antioxidant$_{OH}$ are listed in Table 5.

TABLE 5

Results of in vitro antioxidant indexes of Achyranthis Bidentatae Radix

| Place of origin | ABTS+ free radical scavenging activity (%) | DPPH radical scavenging activity (%) | Hydroxyl radical scavenging activity (U/mL) |
|---|---|---|---|
| Shaanxi Buchang Pharmaceutical Co., Ltd. | 60.00 | 37.27 | 75.56 |
| Shaanxi Xingshengde Pharmaceutical Co., Ltd. | 91.05 | 52.19 | 44.29 |
| Dingzhou City, Hebei | 43.00 | 21.20 | 59.89 |
| Jiabucun, Dafengxiang, Wuzhi County, Henan | 96.50 | 84.03 | 49.06 |
| Tuchengcun, Dahongqiaoxiang, Wuzhi County, Jiaozuo City, Henan | 91.20 | 46.71 | 39.41 |
| Wenxian County, Jiaozuo City, Henan | 52.34 | 30.57 | 58.07 |
| Wenxian County, Jiaozuo City, Henan | 53.28 | 35.73 | 66.40 |
| Wenxian County, Jiaozuo City, Henan | 95.45 | 47.64 | 44.80 |
| Wenxian County, Jiaozuo City, Henan | 20.63 | 19.79 | 34.91 |
| Anguo, Baoding City, Hebei | 32.44 | 26.34 | 30.01 |
| Anguo, Baoding City, Hebei | 22.56 | 19.14 | 30.42 |
| Anguo, Baoding City, Hebei | 95.48 | 43.86 | 48.04 |
| Anguo, Baoding City, Hebei | 26.36 | 20.46 | 37.67 |
| Jiaozuo City, Henan | 94.86 | 52.76 | 47.22 |
| Jiaozuo City, Henan | 53.28 | 29.48 | 60.79 |
| Jiaozuo City, Henan | 32.76 | 22.00 | 77.05 |
| Jiaozuo City, Henan | 26.35 | 20.46 | 37.67 |
| Niujiayingzi Town, Harqin Banner, Chifeng City, Inner Mongolia | 67.86 | 43.63 | 63.30 |
| Niujiayingzi Town, Harqin Banner, Chifeng City, Inner Mongolia | 41.56 | 30.96 | 28.26 |
| Niujiayingzi Town, Harqin Banner, Chifeng City, Inner Mongolia | 21.35 | 38.35 | 45.25 |
| Niujiayingzi Town, Harqin Banner, Chifeng City, Inner Mongolia | 65.38 | 32.34 | 50.87 |

(4) Principal component analysis (PCA): Chromatographic integration data and antioxidant data were imported into multivariate statistical software for PCA. After data alignment, integration, and standardization, the acquired data (n=6) were imported into Simca-p 14.1 software, and PCA was conducted with integral data and bioactivity data as observed values (X). Principal components with the most differential variables were extracted from the resulting data matrix. Eigenvalues and cumulative contribution were obtained from a correlation coefficient matrix R. A model fitted two principal components automatically. Model fitting degree was 79.6%. Contribution of principal component 1 (PC1) was 63.9%, with the most difference information, suggestive of a good fitting ability of the model. The first two principal components were projected, and respective run of data were analyzed by hierarchical clustering analysis (HCA). After preliminary judgment from components load results, chemical index with high contribution of sample difference was β-ecdysterone; in vitro activity indexes included DPPH radical scavenging activity (Antioxidant$_{DPPH}$) and hydroxyl radical scavenging activity (Antioxidant$_{OH}$). Appropriate amount of reference substance (RS) of β-ecdysterone (a principal component in Achyranthis Bidentatae Radix) was weighed accurately in a brown volumetric flask, and prepared into a 1 mg/mL (mass concentration) solution with methanol, respectively; the solution was filtered through a 0.22 μm filter membrane to collect a subsequent filtrate as a reference solution. Content of the identified chemical component was calculated by external standard method of liquid chromatography. Variables were set as: $C_{Ecdysterone}$, Antioxidant$_{DPPH}$, and Antioxidant$_{OH}$.

(5) Functional relationship among chemical component content, antioxidant activity, and experience level corresponding to samples of each training set was established by a binary logistic model. Model expressions are obtained as follows:

$$P_{Excellent} = \frac{\exp\left(\begin{array}{l}-31.020 + 0.146\,Antioxidant_{DPPH} + \\ 0.098\,Antioxidant_{OH} + 222.140C_{Ecdysone}\end{array}\right)}{1 + \exp\left(\begin{array}{l}-31.020 + 0.146\,Antioxidant_{DPPH} + \\ 0.098\,Antioxidant_{OH} + 222.140C_{Ecdysone}\end{array}\right)}$$

$$P_{Good} = \frac{\exp\left(\begin{array}{l}-5.713 + 0.068\,Antioxidant_{DPPH} + \\ 0.023\,Antioxidant_{OH} + 17.3560C_{Ecdysone}\end{array}\right)}{1 + \exp\left(\begin{array}{l}-5.713 + 0.068\,Antioxidant_{DPPH} + \\ 0.023\,Antioxidant_{OH} + 17.3560C_{Ecdysone}\end{array}\right)}$$

$$P_{Fair} = \frac{\exp\left(\begin{array}{l}5.962 - 0.058\,Antioxidant_{DPPH} - \\ 0.006\,Antioxidant_{OH} - 49.559C_{Ecdysone}\end{array}\right)}{1 + \exp\left(\begin{array}{l}5.962 - 0.058\,Antioxidant_{DPPH} - \\ 0.006\,Antioxidant_{OH} - 49.559C_{Ecdysone}\end{array}\right)}$$

$$P_{Poor} = \frac{\exp\left(\begin{array}{l}615.117 - 15.432\,Antioxidant_{DPPH} + \\ 6.252\,Antioxidant_{OH} - 11574.00C_{Ecdysone}\end{array}\right)}{1 + \exp\left(\begin{array}{l}615.117 - 15.432\,Antioxidant_{DPPH} + \\ 6.252\,Antioxidant_{OH} - 11574.00C_{Ecdysone}\end{array}\right)}$$

Measured value of each index was substituted in the above expressions to calculate a probability of which grade an influencing factor belongs to, thereby determining the grade of Achyranthis Bidentatae Radix. Detailed results are listed in Table 6, and probabilities thereof are determined as >87%.

TABLE 6

Grade classification results of *Achyranthis Bidentatae* Radix

| Grade | Place of origin/Original grade | Calculation result |
|---|---|---|
| 4 | Henan/Ungraded | 1.00 |
| 4 | Huaixian County/Ungraded | 1.00 |
| 4 | Unassorted goods/Fair | 1.00 |
| 3 | Inner Mongolia/First grade | 0.99 |
| 3 | Henan/First grade | 1.00 |
| 3 | Hebei/Third grade | 1.00 |
| 3 | Unassorted goods/Good | 1.00 |
| 3 | Shaanxi Xingshengde Pharmaceutical Co., Ltd./Ungraded | 1.00 |
| 3 | Shaanxi Buchang Pharmaceutical Co., Ltd./Ungraded | 1.00 |
| 2 | Inner Mongolia/Unassorted | 0.96 |
| 2 | Henan/Third grade | 1.00 |
| 2 | Henan/Second grade | 0.97 |
| 2 | Unassorted goods/Excellent | 0.93 |
| 2 | Hebei/Ungraded | 1.00 |
| 2 | Inner Mongolia/Unassorted | 0.94 |
| 1 | Unassorted goods/Poor | 1.00 |
| 1 | Hebei/First grade | 0.99 |
| 1 | Inner Mongolia/Second grade | 0.99 |
| 1 | Inner Mongolia/Third grade | 1.00 |
| 1 | Unassorted goods from Hebei/Ungraded | 0.99 |
| 1 | Unassorted goods/Poor | 1.00 |

What is claimed is:

1. A detection method for quality grade of a traditional Chinese medicine (TCM), wherein
    the TCM includes Chinese medicinal materials or herbal slices; and
    the detection method is established by constructing a model of correlation between bioact and the comps of the TCM, the detection method comprising the following steps:
    (1) preparing a TCM test sample;
    (2) determining a comp assay that includes
        a. performing a bioact assay of the TCM test sample; and,
        b. performing a principal comp assay of the TCM test sample; and
    (3) establishing quality grade detection formulas for the TCM using a logistic regression model, the formulas classified into $P_{Ex}$, $P_G$, $P_F$, and $P_p$ as follows, wherein P is in the range of $0 \leq P \leq 1$, where Ex is Excellent, G is Good, F is Fair, P is Poor, act is activity, and comp is component:

$$P_{Ex} = \frac{\exp(\beta_{Ex} + \beta_{Ex\ act\ 1}X_{Ex\ act\ 1} + \beta_{Ex\ act\ 2}X_{Ex\ act\ 2} + \ldots \beta_{Ex\ act\ n}X_{Ex\ act\ n} + \beta_{Ex\ comp\ 1}X_{Ex\ comp\ 1} + \beta_{Ex\ comp\ 2}X_{Ex\ comp\ 2} + \ldots \beta_{Ex\ comp\ n}X_{Ex\ comp\ n})}{1 + \exp(\beta_{Ex} + \beta_{Ex\ act\ 1}X_{Ex\ act\ 1} + \beta_{Ex\ act\ 2}X_{Ex\ act\ 2} + \ldots \beta_{Ex\ act\ n}X_{Ex\ act\ n} + \beta_{Ex\ comp\ 1}X_{Ex\ comp\ 1} + \beta_{Ex\ comp\ 2}X_{Ex\ comp\ 2} + \ldots \beta_{Ex\ comp\ n}X_{Ex\ comp\ n})};$$

$$P_G = \frac{\exp(\beta_G + \beta_{G\ act\ 1}X_{G\ act\ 1} + \beta_{G\ act\ 2}X_{G\ act\ 2} + \ldots \beta_{G\ act\ n}X_{G\ act\ n} + \beta_{G\ comp\ 1}X_{G\ comp\ 1} + \beta_{G\ comp\ 2}X_{G\ comp\ 2} + \ldots \beta_{G\ comp\ n}X_{G\ comp\ n})}{1 + \exp(\beta_G + \beta_{G\ act\ 1}X_{G\ act\ 1} + \beta_{G\ act\ 2}X_{G\ act\ 2} + \ldots \beta_{G\ act\ n}X_{G\ act\ n} + \beta_{G\ comp\ 1}X_{G\ comp\ 1} + \beta_{G\ comp\ 2}X_{G\ comp\ 2} + \ldots \beta_{G\ comp\ n}X_{G\ comp\ n})};$$

$$P_F = \frac{\exp(\beta_F + \beta_{F\ act\ 1}X_{F\ act\ 1} + \beta_{F\ act\ 2}X_{F\ act\ 2} + \ldots \beta_{F\ act\ n}X_{F\ act\ n} + \beta_{F\ comp\ 1}X_{F\ comp\ 1} + \beta_{F\ comp\ 2}X_{F\ comp\ 2} + \ldots \beta_{F\ comp\ n}X_{F\ comp\ n})}{1 + \exp(\beta_F + \beta_{F\ act\ 1}X_{F\ act\ 1} + \beta_{F\ act\ 2}X_{F\ act\ 2} + \ldots \beta_{F\ act\ n}X_{F\ act\ n} + \beta_{F\ comp\ 1}X_{F\ comp\ 1} + \beta_{F\ comp\ 2}X_{F\ comp\ 2} + \ldots \beta_{F\ comp\ n}X_{F\ comp\ n})}; \text{ and,}$$

$$P_P = \frac{\exp(\beta_P + \beta_{P\ act\ 1}X_{P\ act\ 1} + \beta_{P\ act\ 2}X_{P\ act\ 2} + \ldots \beta_{P\ act\ n}X_{P\ act\ n} + \beta_{P\ comp\ 1}X_{P\ comp\ 1} + \beta_{P\ comp\ 2}X_{P\ comp\ 2} + \ldots \beta_{P\ comp\ n}X_{P\ comp\ n})}{1 + \exp(\beta_P + \beta_{P\ act\ 1}X_{P\ act\ 1} + \beta_{P\ act\ 2}X_{P\ act\ 2} + \ldots \beta_{P\ act\ n}X_{P\ act\ n} + \beta_{P\ comp\ 1}X_{P\ comp\ 1} + \beta_{P\ comp\ 2}X_{P\ comp\ 2} + \ldots \beta_{P\ comp\ n}X_{P\ comp\ n})}.$$

2. The detection method of claim 1, wherein
    the preparing of the TCM sample includes the following steps in the recited order:
        weighing approximately 0.3 g of Chinese medicinal materials or herbal slices in a conical flask with cover;
        adding 50 mL of methanol to the conical flask,
        sealing the conical flask tightly;
        weighing the conical flask;
        sonicating the conical flask for 30;
        cooling the conical flask;
        weighing the conical flask again;
        adding methanol to the conical flask to make-up for a weight loss;
        shaking the conical flask well;
        filtering the conical flask; and,
        collecting a subsequent filtrate from the conical flask as a sample solution;
    the determining of the comp assay includes conducting ultra performance liquid chromatography (UPLC) at a characteristic wavelength of the Chinese medicinal materials or herbal slices by using octadecyl silane (ODS) chemically bonded silica as packing the conducting including using 0.1% formic acid-water as mobile phase A and acetonitrile as mobile phase B, conducting gradient elution with a volume ratio of 2% for-the mobile phase B at 0-2 min; a volume ratio of 2% to 100% for the mobile phase B at 2-10 min; a volume ratio of 100% to 2% for the mobile phase B at 10-13 min at; a volume ratio of 2% for the mobile phase B at 13-20 min at 2%; a volume flow of 0.2 mL/min; a column temperature of 25° C.; and, an injection volume of 2 μL.

3. The detection method of claim 2, wherein the performing of the bioact assay includes detecting ABTS$^+$ free radical scavenging act (%), DPPH radical scavenging act (%), and hydroxyl radical scavenging act.

4. The detection method of claim 3, wherein the performing of the principal comp assay includes a principal comp analysis (PCA) and a hierarchical clustering analysis (HCA).

5. The detection method of claim 4, wherein the TCM is any one of Cinnamomi Ramulus, Salviae Miltiorrhizae Radix et Rhizoma, or Achyranthis Bidentatae Radix.

6. The detection method of claim 5, wherein the quality grade detection formulas for Cinnamomi Ramulus are as follows, where Antiox is Antioxidant, Cin is Cinnamaldehyde, Cinac is Cinnamic acid, Cinalc is Cinnamyl alcohol, and Coum is Coumarin:

$$P_{Ex} = \frac{\exp(-0.974 Antiox_{DPPH} + 2.197 Antiox_{OH} - 0.96 C_{Cin} + 10.158 C_{Cinac} + 44.7 C_{Cinalc} - 43.222 C_{Coum} + 32.543)}{1 + \exp(-0.974 Antiox_{DPPH} + 2.197 Antiox_{OH} - 0.96 C_{Cin} + 10.158 C_{Cinac} + 44.7 C_{Cinalc} - 43.222 C_{Coum} + 32.543)};$$

$$P_G = \frac{\exp(2.545 Antiox_{DPPH} - 0.744 Antiox_{OH} - 0.827 C_{Cin} - 35.909 C_{Cinac} - 91.409 C_{Cinalc} + 117.883 C_{Coum} - 449.205)}{1 + \exp(2.545 Antiox_{DPPH} - 0.744 Antiox_{OH} - 0.827 C_{Cin} - 35.909 C_{Cinac} - 91.409 C_{Cinalc} + 117.883 C_{Coum} - 449.205)};$$

$$P_F = \frac{\exp(1.093 Antiox_{DPPH} - 1.521 Antiox_{OH} + 1.343 C_{Cin} + 31.391 C_{Cinac} + 22.043 C_{Cinalc} + 6.076 C_{Coum} - 196.728)}{1 + \exp(1.093 Antiox_{DPPH} - 1.521 Antiox_{OH} + 1.343 C_{Cin} + 31.391 C_{Cinac} + 22.043 C_{Cinalc} + 6.076 C_{Coum} - 196.728)}; \text{ and,}$$

$$P_P = \frac{\exp(-0.875 Antiox_{DPPH} + 0.892 Antiox_{OH} - 0.952 C_{Cin} - 33.664 C_{Cinac} - 20.326 C_{Cinalc} - 9.724 C_{Coum} + 199.880)}{1 + \exp(-0.875 Antiox_{DPPH} + 0.892 Antiox_{OH} - 0.952 C_{Cin} - 33.664 C_{Cinac} - 20.326 C_{Cinalc} - 9.724 C_{Coum} + 199.880)}.$$

7. The detection method of claim 5, wherein the quality grade detection formulas for Salviae Miltiorrhizae Radix et Rhizoma are as follows, where Tan is Tanshinone IIA, Sal is Salvianolic acid, and Antiox is Antioxidant:

$$P_{Ex} = \frac{\exp(-12.692 + 1.571 C_{Tan} - 1.056 C_{Sal} + 1.272 Antiox_{DPPH} - 0.152 Antiox_{OH})}{1 + \exp(-12.692 + 1.571 C_{Tan} - 1.056 C_{Sal} + 1.272 Antiox_{DPPH} - 0.152 Antiox_{OH})};$$

$$P_G = \frac{\exp(118.369 - 3.453 C_{Tan} + 0.642 C_{Sal} - 5.175 Antiox_{DPPH} + 0.645 Antiox_{OH})}{1 + \exp(118.369 - 3.453 C_{Tan} + 0.642 C_{Sal} - 5.175 Antiox_{DPPH} + 0.645 Antiox_{OH})};$$

$$P_F = \frac{\exp(69.307 - 12.857 C_{Tan} + 1.326 C_{Sal} - 0.771 Antiox_{DPPH} - 1.160 Antiox_{OH})}{1 + \exp(69.307 - 12.857 C_{Tan} + 1.326 C_{Sal} - 0.771 Antiox_{DPPH} - 1.160 Antiox_{OH})}; \text{ and}$$

$$P_P = \frac{\exp(-89.539 + 3.845 C_{Tan} + 1.166 C_{Sal} - 0.240 Antiox_{DPPH} + 0.119 Antiox_{OH})}{1 + \exp(-89.539 + 3.845 C_{Tan} + 1.166 C_{Sal} - 0.240 Antiox_{DPPH} + 0.119 Antiox_{OH})}.$$

8. The detection method for quality grade of TCM according to claim 5, wherein quality grade detection formulas of the Achyranthis Bidentatae Radix are as follows, where Antiox is Antioxidant:

$$P_{Ex} = \frac{\exp(-31.020 + 0.146 Antiox_{DPPH} + 0.098 Antiox_{OH} + 222.140 C_{Ecdysone})}{1 + \exp(-31.020 + 0.146 Antiox_{DPPH} + 0.098 Antiox_{OH} + 222.140 C_{Ecdysone})};$$

$$P_G = \frac{\exp(-5.713 + 0.068 Antiox_{DPPH} + 0.023 Antiox_{OH} + 17.3560 C_{Ecdysone})}{1 + \exp(-5.713 + 0.068 Antiox_{DPPH} + 0.023 Antiox_{OH} + 17.3560 C_{Ecdysone})};$$

$$P_F = \frac{\exp(5.962 - 0.058 Antiox_{DPPH} - 0.006 Antiox_{OH} - 49.559 C_{Ecdysone})}{1 + \exp(5.962 - 0.058 Antiox_{DPPH} - 0.006 Antiox_{OH} - 49.559 C_{Ecdysone})}; \text{ and,}$$

$$P_P = \frac{\exp(615.117 - 15.432 Antiox_{DPPH} + 6.252 Antiox_{OH} - 11574.00 C_{Ecdysone})}{1 + \exp(615.117 - 15.432 Antiox_{DPPH} + 6.252 Antiox_{OH} - 11574.00 C_{Ecdysone})}.$$

\* \* \* \* \*